US00PP20882P2

(12) United States Plant Patent
van Gaalen et al.

(10) Patent No.: US PP20,882 P2
(45) Date of Patent: Mar. 23, 2010

(54) ***ERYNGIUM* PLANT NAMED 'EPTJ'**

(50) Latin Name: *Eryngium planum*
Varietal Denomination: EPTJ

(76) Inventors: René van Gaalen, Sionsweg 26, 2286 KL Rijswijk (NL); Huibert Anne de Boer, Collegiantenstraat 90, 2231 HM Rijnsburg (NL)

( * ) Notice: Subject to any disclaimer, the term of this patent is extended or adjusted under 35 U.S.C. 154(b) by 0 days.

(21) Appl. No.: 12/283,264

(22) Filed: Sep. 8, 2008

(51) Int. Cl.
*A01H 5/00* (2006.01)

(52) U.S. Cl. ..... Plt./361

(58) Field of Classification Search ..... Plt./361, Plt./263.1
See application file for complete search history.

(56) References Cited

U.S. PATENT DOCUMENTS

PP18,942 P2 * 6/2008 de Boer ..... Plt./361

OTHER PUBLICATIONS

Tom Atwell. Maine Gardener: Beginning gardeners needn't worry about botanical names. Portland Press Herald. Feb. 22, 2009.*

* cited by examiner

*Primary Examiner*—Wendy C Haas
(74) *Attorney, Agent, or Firm*—C. A. Whealy

(57) ABSTRACT

A new and distinct cultivar of *Eryngium* plant named 'EPTJ', characterized by its compact and upright plant habit; moderately vigorous growth habit; freely branching habit; and single blue-colored flowers arranged on dense flower heads.

2 Drawing Sheets

Botanical designation: *Eryngium planum*
Cultivar denomination: 'EPTJ'

BACKGROUND OF THE INVENTION

The present invention relates to a new and distinct cultivar of *Eryngium* plant, botanically known as *Eryngium planum,* and hereinafter referred to by the name 'EPTJ'.

The new *Eryngium* plant was discovered by the Inventors in a controlled outdoor nursery environment in Rijswijk, The Netherlands, in April, 2007, as a naturally-occurring whole plant mutation of the *Eryngium planum* 'Paradise Jackpot', disclosed in U.S. Plant Pat. No. 18,942. The new *Eryngium* plant was observed as a single plant from within a population of plants of 'Paradise Jackpot'. The selection of this plant was based on its unique inflorescence form.

Asexual reproduction of the new *Eryngium* plant by cuttings in a controlled environment in Rijswijk, The Netherlands since June, 2007, has shown that the unique features of this new *Eryngium* plant are stable and reproduced true to type in successive generations.

SUMMARY OF THE INVENTION

Plants of the new *Eryngium* have not been observed under all possible environmental conditions. The phenotype may vary somewhat with variations in environment such as temperature and light intensity, without, however, any variance in genotype.

The following traits have been repeatedly observed and are determined to be the unique characteristics of 'EPTJ'. These characteristics in combination distinguish 'EPTJ' as a new and distinct cultivar of *Eryngium:*

1. Compact and upright plant habit.
2. Moderately vigorous growth habit.
3. Freely branching habit.
4. Single blue-colored flowers on dense flower heads.

Plants of the new *Eryngium* differ from plants of the parent, 'Paradise Jackpot' in the following characteristics:

1. Plants of the new *Eryngium* are more compact than plants of 'Paradise Jackpot'.
2. Plants of the new *Eryngium* are easier to propagate than plants of 'Paradise Jackpot'.

Plants of the new *Eryngium* can also be compared to plants of the *Eryngium planum* 'Blue Hobit', not patented. Plants of the new *Eryngium* differ from plants of 'Blue Hobit' primarily in plant habit as plants of the new *Eryngium* are more uniform in plant habit than plants of 'Blue Hobit'.

BRIEF DESCRIPTION OF THE PHOTOGRAPHS

The accompanying photographs illustrate the overall appearance of the new *Eryngium* plant. The photographs show the colors as true as it is reasonably possible to obtain in colored reproductions of this type. Colors in the photographs may differ slightly from the color values cited in the detailed botanical description which accurately describe the colors of the new *Eryngium* plant. The photograph on the first sheet comprises a side perspective view of a typical flowering plant of 'EPTJ' grown in an outdoor nursery. The photograph at the top of the second sheet is a close-up view of a typical inflorescence of 'EPTJ'. The photograph at the bottom of the second sheet is a close-up view of a typical leaf of 'EPTJ'.

DETAILED BOTANICAL DESCRIPTION

The aforementioned photographs and following observations and measurements describe plants grown in Rijswijk, The Netherlands during the summer in an outdoor nursery and under conditions and practices which approximate those generally used in commercial *Eryngium* production. During the production of the plants, day temperatures ranged from 12° C. to 28° C. and night temperatures ranged from 4° C. to 15° C. Measurements and numerical values represent averages for typical flowering plants. Plants had been growing for one year when the photographs and description were taken. In the following description, color references are made to The Royal Horticultural Society Colour Chart, 2001 Edition, except where general terms of ordinary dictionary significance are used.

Botanical classification *Eryngium planum* 'EPTJ'.

Parentage: Naturally-occurring whole plant mutation of *Eryngium planum* 'Paradise Jackpot', disclosed in U.S. Plant Pat. No. 18,942.

Propagation:

*Type.*—By cuttings.

*Time to initiate roots.*—About 80 days at 12° C.

*Time to produce a rooted young plant.*—About six months at 18° C.

*Root description.*—Fibrous, fleshy and thick; white in color.

*Rooting habit.*—Freely branching; dense.

Plant description:

*Plant form/growth habit.*—Herbaceous perennial; compact and upright plant habit; freely branching with about eleven lateral branches developing per plant. Moderately vigorous growth habit.

*Plant height.*—About 36.8 cm.

*Plant diameter or spread.*—About 31.8 cm.

*Lateral branches.*—Length: About 8.1 cm. Diameter: About 2.5 mm. Internode length: About 1.7 cm. Aspect: Mostly upright to slightly outward. Strength: Strong. Texture: Smooth, glabrous. Color: Between 147C and 148B; tinged with 92B.

Foliage description:

*Arrangement.*—Alternate, simple; sessile.

*Length, stem leaves.*—About 5.4 cm.

*Length, basal leaves.*—About 8.2 cm.

*Width, stem leaves.*—About 4.8 cm.

*Width, basal leaves.*—About 7.4 cm.

*Shape, stem leaves.*—Palmately lobed.

*Shape, basal leaves.*—Obovate.

*Apex, stem leaves.*—Mucronate.

*Apex, basal leaves.*—Mucronulate.

*Base, stem and basal leaves.*—Hastate.

*Margin, stem leaves.*—Serrate.

*Margin, basal leaves.*—Crenate.

*Texture, stem and basal leaves, upper and lower surfaces.*—Smooth, glabrous; leathery.

*Venation pattern, stem and basal leaves.*—Pinnate.

*Color, stem and basal leaves.*—Developing leaves, upper surface.—Close to 137B. Developing leaves, lower surface: Close to 138A. Fully expanded leaves, upper surface: Close to 137A to 137B; venation, close to 145D. Fully expanded leaves, lower surface: Close to 138A; venation, close to 138A.

Flower description:

*Flower arrangement and habit.*—Single rotate flowers arranged on dense ovoid flower heads; flowers sessile. Inflorescences arising from leaf axils. Freely flowering habit with usually about 300 flowers developing per inflorescence. Flowers face upright and outwardly.

*Fragrance.*—Faint; unpleasant.

*Natural flowering season.*—Plants of the new *Eryngium* initiate and develop flowers during the late summer and flower continuously from August through October in The Netherlands.

*Flower longevity.*—Flowers last about two weeks on the plant and about twelve days as a cut flower; flowers persistent.

*Inflorescence height.*—About 4.5 cm.

*Inflorescence diameter.*—About 2.6 cm.

*Flower diameter.*—About 3 mm.

*Flower length (depth).*—About 5 mm.

*Flower bud.*—Shape: Obovate. Length: About 3 mm. Diameter: About 1.5 mm. Color: Close to 145B.

*Petals.*—Arrangement: Five petals in a single whorl. Length: About 1.8 mm. Width: About 1 mm. Shape: Elliptic. Apex: Acute; recurved. Margin: Entire. Texture, upper and lower surfaces: Smooth, glabrous. Color: When opening, upper and lower surfaces: Close to 97B to 97C. Fully opened, upper and lower surfaces: Close to 96A; color becoming closer to 98C to 98D with development.

*Sepals.*—Arrangement: Five sepals in a single whorl. Length: About 3 mm. Width: About 1.5 mm. Shape: Ovate. Apex: Acute. Base: Cuneate. Margin: Entire. Texture, upper and lower surfaces: Smooth, glabrous. Color, immature, upper and lower surfaces: Close to 145B. Color, mature, upper and lower surfaces: Close to 144A to 144B.

*Inflorescence bracts.*—Arrangement: About twelve bracts in a single whorl subtending the flower head. Length: About 1.5 cm. Width: About 7 mm. Shape: Ovate. Apex: Apiculate. Base: Cuneate. Margin: Entire. Texture, upper and lower surfaces: Smooth, glabrous. Color, immature and mature, upper and lower surfaces: Between 147C and 148B strongly tinged with close to 92B; midvein, close to 91C to 91D.

*Peduncles.*—Length: About 7.7 cm. Diameter: About 2 mm. Angle: Main peduncle, erect; lateral peduncles, about 30° from vertical. Strength: Strong. Texture: Smooth, glabrous. Color: Between 147C and 148B; tinged with 96D.

*Reproductive organs.*—Stamens: Quantity/arrangement: About four per flower. Anther shape: Ovate. Anther length: About 1 mm. Anther color: Close to N92B. Filament length: About 2.5 mm. Filament color: Close to 97A. Pollen amount: Moderate. Pollen color: Close to 156D.

*Pistils.*—Quantity: About two per flower. Pistil length: About 3 mm. Style length: About 2.8 mm. Style color: Close to 95D to lighter than 95D. Stigma shape: Rounded. Stigma color: Close to 95D to lighter than 95D. Ovary color: Close to 144B to 144C. Fruits/seeds: Fruit and seed development have not been observed.

Disease/pest resistance: Plants of the new *Eryngium* have not been shown to be resistant to pathogens and pests common to *Eryngium*.

Garden performance: Plants of the new *Eryngium* have exhibited good tolerance to rain and wind, have been observed to tolerate temperatures from about −15° C. to about 35° C.

It is claimed:

1. A new and distinct *Eryngium* plant named 'EPTJ' as illustrated and described.

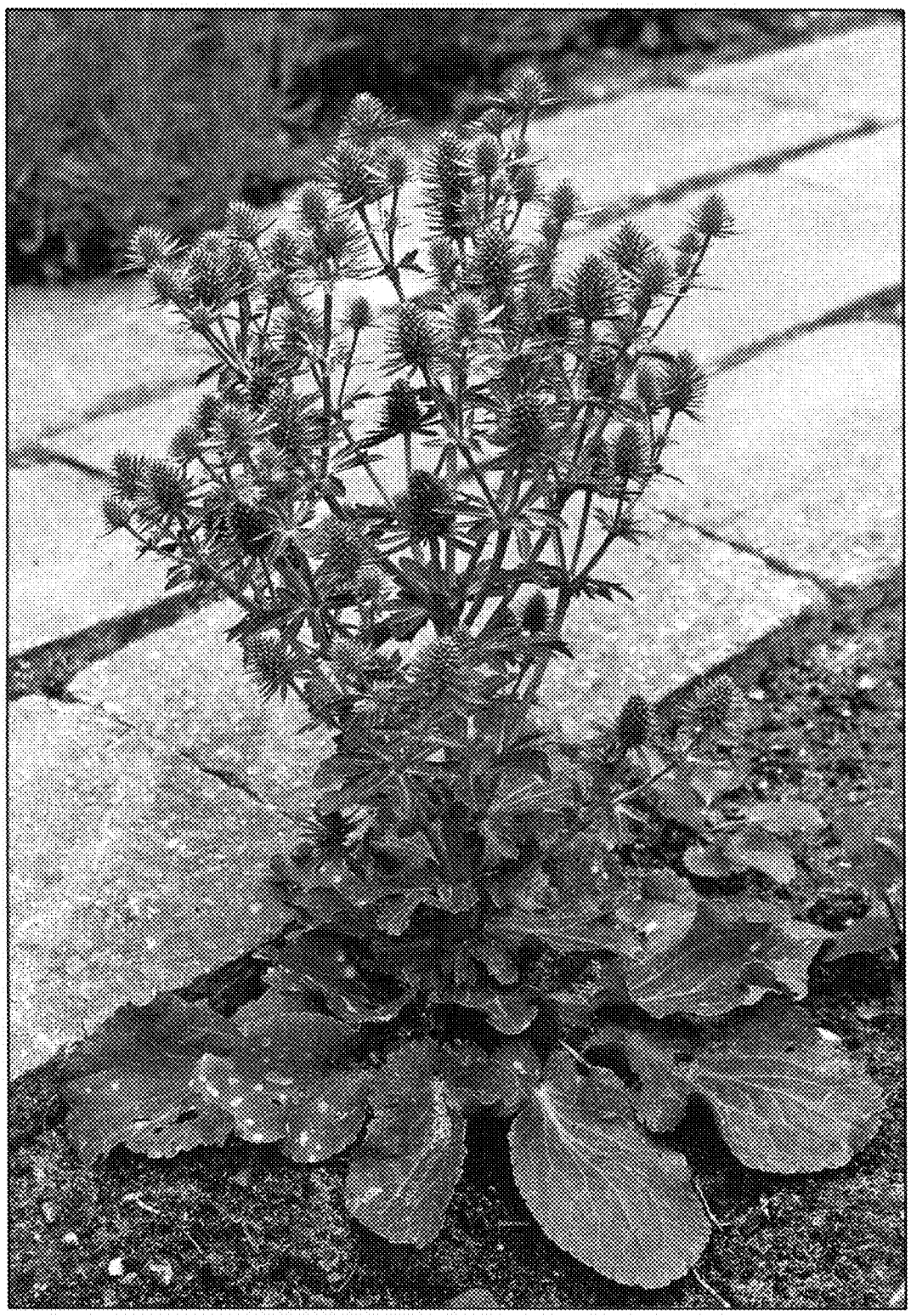

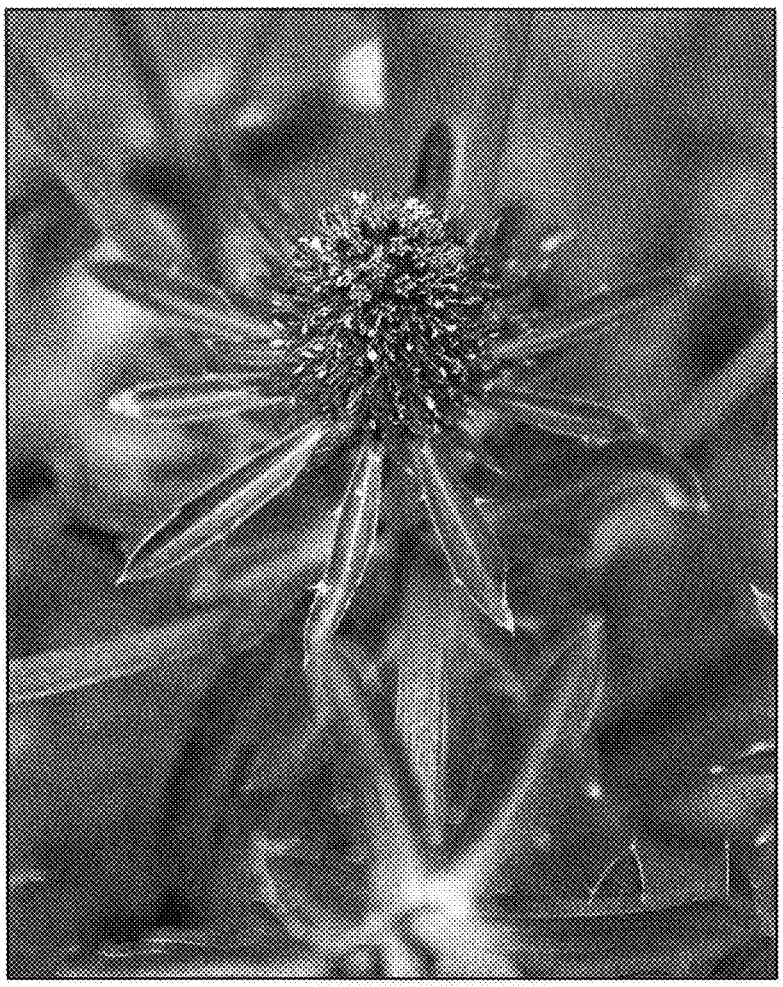
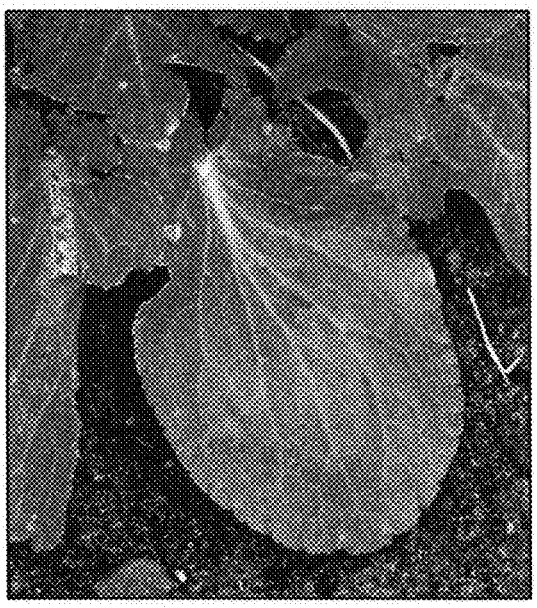

* * * * *